(12) United States Patent
Kese et al.

(10) Patent No.: US 6,206,877 B1
(45) Date of Patent: Mar. 27, 2001

(54) COMBINED BIPOLAR SCISSOR AND GRASPER AND METHOD OF FORMING THEREOF

(75) Inventors: Kelly Kese, Goode, VA (US); Donald W. Regula, Belle Mead, NJ (US)

(73) Assignee: Ethicon, Inc., Somerville, NJ (US)

( * ) Notice: Subject to any disclaimer, the term of this patent is extended or adjusted under 35 U.S.C. 154(b) by 0 days.

(21) Appl. No.: 09/410,384

(22) Filed: Sep. 30, 1999

Related U.S. Application Data (63) Continuation-in-part of application No. 08/919,432, filed on Aug. 27, 1997, now Pat. No. 6,024,744.

(51) Int. Cl.[7] .................................................. A61B 18/18
(52) U.S. Cl. ................................. 606/48; 606/51; 606/41
(58) Field of Search .................................. 606/41, 45, 46, 606/48–52, 205–207

(56) References Cited

U.S. PATENT DOCUMENTS

| | | | |
|---|---|---|---|
| 3,651,811 | * | 3/1972 | Hildebrandt et al. . |
| 5,324,289 | * | 6/1994 | Eggers .................................... 606/48 |
| 5,827,281 | * | 10/1998 | Levin ..................................... 606/51 |
| 5,984,938 | * | 11/1999 | Yoon ..................................... 606/170 |

\* cited by examiner

Primary Examiner—Linda C. M. Dvorak
Assistant Examiner—Roy Gibson
(74) Attorney, Agent, or Firm—Scully, Scott, Murphy & Presser (57) ABSTRACT

A method of forming a combination bipolar scissors and graspers surgical instrument. The method has the steps of: providing a predetermined blade configuration of a bipolar scissors surgical instrument, the predetermined blade configuration having first and second jaw members each having a respective first and second cutting edge and first and second pivoting surfaces; defining a first grasping surface on the first jaw member, the first grasping surface being distal to the cutting edge, the first grasping surface being contained within the confines of the predetermined blade configuration; defining a second grasping surface opposing the first grasping surface on the second jaw member, the second grasping surface being contained within the confines of the predetermined blade configuration; providing a pivot pin pivotally connected to the jaw members wherein at least one jaw member is pivotable in relation to the other jaw member about the pivoting surfaces, the jaw members being capable of pivoting between an open and closed position such that the cutting edges form a scissor and the grasping surfaces form a clamp when the jaw members are in their closed position; and electrically isolating the first jaw member from the second jaw member. A further method is provided in which the cutting edges are distal to the grasping surfaces. Also provided are combination scissors/graspers having blade configurations as illustrated in FIGS. 12A–B to 14A–B.

22 Claims, 10 Drawing Sheets

COMBINED BIPOLAR SCISSOR AND GRASPER AND METHOD OF FORMING THEREOF

This application is a continuation-in-part of Ser. No. 08/919,432 Aug. 27, 1997 now U.S. Pat. No. 6,024,744.

BACKGROUND OF THE INVENTION

1. Field of the Invention

The field of art to which this invention relates is surgical instruments, in particular, electrosurgical cutting and grasping instruments.

2. Description of the Related Art

Surgery requires the use of surgical instruments within a restricted and unusually sensitive operating field. During surgery, the field becomes crowded if a large number of surgical instruments must be used simultaneously, with concomitant difficulty for the surgical team to maintain a clear viewing area. Under such circumstances, surgical instruments designed to perform more than one task are of particular importance.

Two techniques used extensively in both open and endoscopic surgery are (a) the controlling of bleeding using electrosurgical instrumentation and (b) the incision or severing of tissue or vessels. The control of bleeding during surgery accounts for a major portion of the time involved in surgery. In particular, bleeding that occurs when tissue is incised or severed can obscure the surgeon's vision, prolong the operation, and adversely effect the precision of cutting. Blood loss from surgical cutting may require blood infusion, thereby increasing the risk of harm to the patient.

Hemostatic electrosurgical techniques are known in the art for reducing bleeding from incised tissue prior to, during, and subsequent to incision. Electrosurgical cutting and coagulating instruments are used to perform such techniques. These instruments can be of a reusable type (which require cleaning and disinfecting or sterilizing before each use) or disposable (which are disposed of after a single use). Each type includes both monopolar and bipolar variations having at least one electrode. Radio frequency (RF) energy is conducted through this electrode to either a remote conductive body-plate (known as a grounding pad) in the case of monopolar instruments, or to a second, closely spaced conductive electrode in the case of bipolar instruments. In monopolar instruments electrical current travels from the electrode through the patient's body to the grounding pad. Bipolar instruments are typically connected to both poles of an electrosurgical generator, therefore current flow is typically limited to tissue adjacent to the working end of the bipolar instrument (where the two electrodes are located).

Prior to the advent of electrosurgical cutting instruments, a surgeon would perform any cutting with a scissors and coagulate with an entirely different instrument. This exchange of instrumentation was time consuming. In response for the need to have a scissors-type instrument for cutting but which also incorporated the ability to coagulate blood and other body tissue using RF energy, electrosurgical cutting devices have been developed which combine mechanical cutting with electrosurgical cauterization, coagulation, and cutting.

Standard shape and size scissors have evolved in the surgical arts which surgeons have become accustomed to. These standards have been incorporated into the electrosurgical cutting instruments, not only because they have been tested by time and found to be very functional, but mainly because surgeons have become accustomed with their feel and use. Examples of some of these standards include the Mayo, Metzenbaum, and Tenotomy scissors. Each standard scissor is typically available in both curved and straight variations.

Grasper or forcep type instruments are also well known in the art. They generally consist of opposing jaws which pivot about a pivot point into an open or closed position. In a closed position the jaws of the grasper provide a means to grasp and hold, or grasp and tear, a piece of body organ, a vessel, or tissue.

Electrosurgical graspers have been developed to cauterize a portion of tissue. This is accomplished in one of two ways. Cauterization can be accomplished by using an outside surface or the tip of both jaws to cauterize the tissue the jaws contact. Cauterization can also be accomplished with a grasper by grasping down onto tissue and cauterizing the tissue between the jaws. It is in this way that electrosurgical graspers are used to coapt a vessel prior to transection with a cutting device. Electrosurgical graspers are also used to coapt retracted bleeders (severed blood vessels).

In practice, vessels are coapted in several ways. One such way is by using a standard grasper not capable of cauterization and a monopolar pencil. The vessel is first clamped between the jaws of the grasper, and the pencil is used to energize the grasper with RF energy. The RF energy passes from the monopolar pencil, through the forceps, vessel and patients body to the grounding pad. This is a potentially dangerous procedure. The patient or surgeon can be easily injured in such a procedure.

Another way to perform coaptation of vessels is by using a monopolar or bipolar scissors in which the scissors are rotated exposing the vessel to the side surfaces of the scissor's blades. In theory, the blade sides cauterize the vessel and the vessel is then severed with the scissors. In practice, this procedure is very difficult and can lead to complications. It is very easy for a surgeon to nick the vessel with the scissor blades before the coaptation of the vessel is complete, causing unanticipated bleeding and the need for further instrumentation to stop the bleeding.

Whichever method of coaptation is used, subsequent to the coaptation, the vessel is severed by a cutting instrument such as an electrosurgical scissor. In light of the above discussion, this procedure has been most effectively and safely accomplished with at least two different surgical instruments, a grasper to grasp and coapt, and a scissor to sever the coapted vessel.

Tidemand, U.S. Pat. No. 5,342,381, discloses an endoscopic combination bipolar scissors and forceps instrument which has blade and forceps portions on each of two jaws. Although the Tidemand instrument is useful it is subject to several disadvantages which effect the performance of the device, especially with regard to coaptation of vessels.

Since the blades of the Tidemand invention are insulated (typically ceramic) the blades themselves only offer mechanical cutting. As discussed previously, an instrument which offers both mechanical and electrosurgical cutting is preferred over one which offers only the former. Additionally, certain procedures require that the scissors portion of the instrument be distal to the graspers. Likewise, some procedures require the grasper portion of the instrument to be distal to the scissor portion. Tidemand discloses only the latter configuration, which is inadequate in many surgical procedures.

Furthermore, the shape and size of the cutting and grasping surfaces in the Tidemand instrument are awkward, unlike any standard scissor that surgeons have become accustomed to.

With regard to surgical procedures in which coaptation of vessels is required, the Tidemand combination instrument could not be effectively utilized. Effective coaptation requires hemostasis during cutting as well as during grasping (or clamping) in order to cauterize the ends of the severed vessel.

Like the Tidemand instrument, the single feature electrosurgical cutting devices and graspers of the prior art are useful and effective, but they too suffer from several deficiencies associated with their use. The instrument exchange associated with cutting, coagulating and coaptation requires dexterity on the part of the surgeon. The increased number of instruments has the disadvantage of crowding the operating field. Additionally, there is a greater burden on assistant personnel in the operating room, such as nurses, because of the exchange of instrumentation between them and the surgeon.

Another disadvantage of the prior art concerns cleaning, disinfecting and sterilization (CDS) issues known in the surgical instrumentation art. Transmission of sickness and disease through contaminated instrumentation is a very real problem in the medical field. Typically, surgical instrumentation is cleaned and disinfected or sterilized after each use to minimize this possibility. Since effective coaptation of vessels has required two instruments, a graspers and a scissors, the risk of disease transmission is increased. The explanation for this is purely statistical, the probability of transmitting disease in two instruments is greater than for a single instrument.

Additionally, the cost of processing (cleaning, disinfecting or sterilizing) two reusable instruments and purchasing two reusable instruments is greater than the costs associated with a single combined instrument.

To combat the CDS problems associated with reusable instruments, disposable instruments have been developed which are disposed after a single use. While they have their advantages, disposable instruments suffer from the disadvantage of contributing to the amount of medical waste generated.

The prior art disposable scissors and graspers suffer the disadvantage of contributing twice the medical waste as a single disposable instrument combining both features. Likewise, the cost of two disposable surgical instruments is greater than the cost of a combined disposable instrument.

Accordingly, there is a need in the art for an improved electrosurgical instrument having mechanical grasping and cauterization capabilities to coapt vessels combined with capabilities to mechanically transect and cauterize the vessel, contained within a standard scissors shape and size.

SUMMARY OF THE INVENTION

Therefore, it is an object of the present invention to provide a single bipolar electrosurgical instrument and method for forming thereof which is capable of performing the functions of both a bipolar forceps and a bipolar scissors.

It is yet a further object of the present invention to provide a single bipolar electrosurgical instrument and method for forming thereof which combines a bipolar scissors and bipolar grasper with the grasping portions contained within a standard scissor shape and size.

It is yet a further object of the present invention to provide a single bipolar electrosurgical instrument and method for forming thereof to eliminate the need to energize a standard grasper with a monopolar pencil.

It is yet a further object of the present invention a single bipolar electrosurgical instrument and method for forming thereof to eliminate the need to rotate a monopolar or bipolar scissors to coapt a vessel.

It is yet another object of the present invention to provide a single bipolar electrosurgical instrument and method for forming thereof which provides for improved cauterization and coagulation.

It is yet another object of the present invention to provide a single bipolar electrosurgical instrument and method for forming thereof which reduces the amount of instrumentation necessary for surgical procedures in which both electrosurgical cutting and grasping is required.

It is yet another object of the present invention to provide a single bipolar electrosurgical instrument and method for forming thereof which reduces the burden on assistant personnel in an operating room in which a surgical procedure is being performed that requires both electrosurgical cutting and grasping.

It is yet another object of the present invention to provide a single bipolar electrosurgical instrument and method for forming thereof which reduces the amount of dexterity needed by a surgeon performing a surgical procedure in which both electrosurgical cutting and grasping is required.

It is yet another object of the present invention to provide a single bipolar electrosurgical instrument and method for forming thereof which reduces the costs associated with surgical procedures in which both electrosurgical cutting and grasping is required.

It is yet another object of the present invention to provide a single bipolar electrosurgical instrument and method for forming thereof which decreases the probability of transmission of disease due to contaminated instrumentation in surgical procedures in which both electrosurgical cutting and grasping is required.

It is still yet another object of the present invention to provide a single bipolar electrosurgical instrument and method for forming thereof which decreases the amount of medical waste generated in surgical procedures in which both electrosurgical cutting and grasping is required.

Accordingly, a method of forming a combination bipolar scissors and graspers surgical instrument is provided. The method comprises the steps of: providing a predetermined blade configuration of a bipolar scissors surgical instrument, the predetermined blade configuration having first and second jaw members each having a respective first and second cutting edge and first and second pivoting surfaces; defining a first grasping surface on the first jaw member, the first grasping surface being distal to the cutting edge, the first grasping surface being contained within the confines of the predetermined blade configuration; defining a second grasping surface opposing the first grasping surface on the second jaw member, the second grasping surface being contained within the confines of the predetermined blade configuration; providing a pivot pin pivotally connected to the jaw members wherein at least one jaw member is pivotable in relation to the other jaw member about the pivoting surfaces, the jaw members being capable of pivoting between an open and closed position such that the cutting edges form a scissor and the grasping surfaces form a clamp when the jaw members are in their closed position; and electrically isolating the first jaw member from the second jaw member.

In another embodiment of the methods of the present invention, the cutting edges are distal to the grasping surfaces.

Figure 12A:
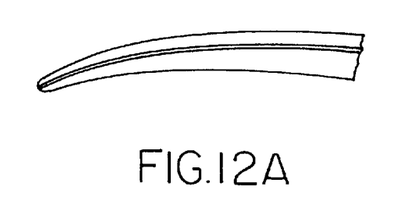
FIGS. 12A and 12B illustrate a plan and front view, respectively, of a standard Mayo surgical scissor.
Figure 12B:
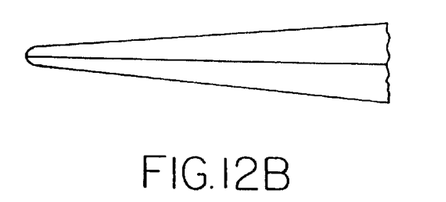

In yet other embodiments of the present invention bipolar electrosurgical instruments are provided having a combined scissor and grasper, wherein the scissor and grasper are formed within the shape of the standard scissors illustrated in FIGS. 12A, 12B; 13A, 13B; and 14A, 14B.

BRIEF DESCRIPTION OF THE DRAWINGS

These and other features, and advantages of the methods of the present invention will become better understood with regard to the following description, appended claims, and accompanying drawings where:

DETAILED DESCRIPTION OF THE PREFERRED EMBODIMENTS

Figure 1A:
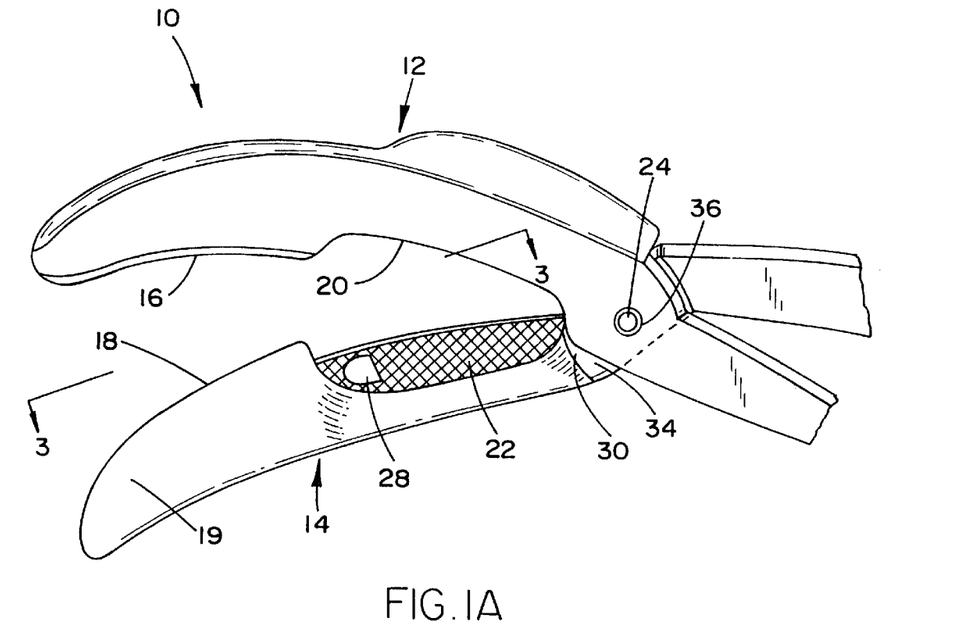
FIG. 1A illustrates an isometric view of the operating end of an embodiment of the present invention in which the scissors portion is distal, the jaw members thereof being shown in an opened position.
Figure 1B:
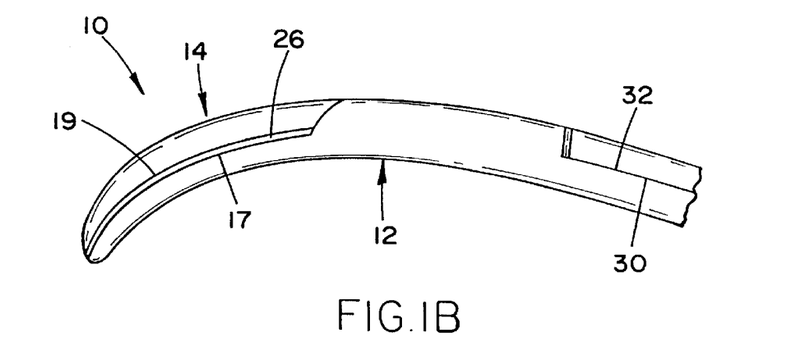
FIG. 1B illustrates the top view of the embodiment illustrated in FIG. 1A, the jaw members thereof being shown in a closed position.

Referring now in detail to FIGS. 1A and 1B there is illustrated the operating (or distal) end of the inventive combined bipolar scissors and grasper instrument 10 which includes first and second jaw members 12,14. Each jaw member having a cutting edge 16,18, a cutting surface 17,19, and a grasping surface 20,22. The cutting edges 16,18 and grasping surfaces 20,22 generally being formed of a conductive material, preferably stainless steel. The first cutting edge 16 opposes the second cutting edge 18 and the first grasping surface 20 opposes the second grasping surface 22.

The first jaw member 12 further has a first pivoting surface 30. The second jaw member 14 further has a second pivoting surface 32. The pivoting surfaces 30,32 slidably contact each other at a point where the jaw members 12,14 intersect.

The jaw members 12,14 are pivotally connected by way of a rivet, screw, or pin 24 at their point of intersection such that they are capable of pivoting between an open and closed position. The point of intersection is configured with a conventional surgical scissors pivot.

Figure 1C:
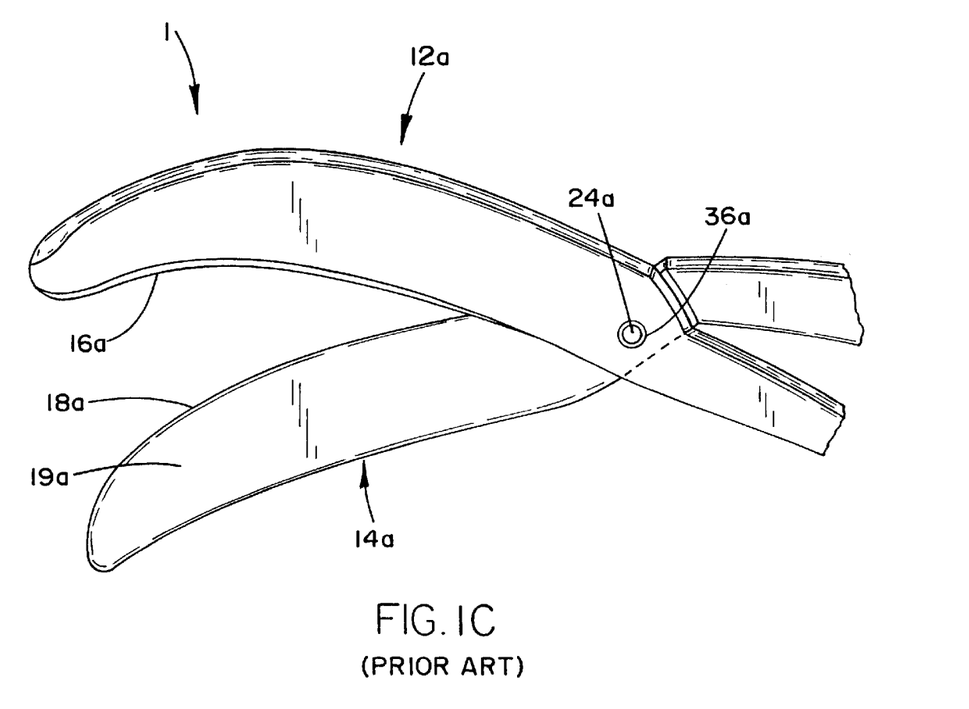
FIG. 1C illustrates an isometric view of the operating end of a typical bipolar surgical scissors of the prior art, the blade members thereof being shown in an opened position.
Figure 1D:
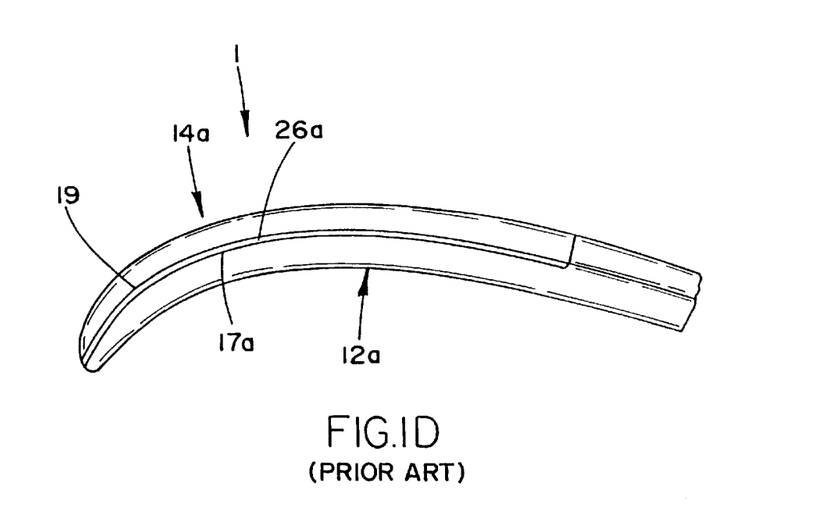
FIG. 1D illustrates the top view of the embodiment illustrated in FIG. 1C, the blade members thereof being shown in a closed position.

As shown in FIGS. 1C and 1D, a conventional bipolar surgical scissor is shown having a predetermined blade configuration and referred to generally as reference numeral 1, wherein a first blade member 12a pivots about a second blade member 14a whereby they are retained into a pivoting relationship by a rivet, pin or screw 24a. The predetermined blade configuration can be any of those previously discussed, such as those having a Mayo, Metzenbaum, or Tenotomy configuration, or any other blade configuration now know or later developed.

Each blade member has a cutting edge 16a,18a and a cutting surface 17a,19a. A first electrically insulating coating 26a is applied to the first cutting surface 17a and a second insulating coating 36a is applied to the pin 24a for electrically isolating the first blade member 12a from the second blade member 14a. Therefore, electrical conduction is prevented from the first jaw member 12a to the second jaw member 14a through the rivet, pin or screw 24a.

Referring back to FIGS. 1A and 1B, when in the closed position, the first cutting edge 16 engages the second cutting edge 18 in a shearing motion. Similarly, the first grasping surface 20 substantially meets the second grasping surface 22 to form a clamp for grasping and clamping tissue or vessels therewithin.

Electrically insulating material is provided to electrically isolate the first jaw member 12 from the second jaw member 14. A first electrically insulating coating 26 is secured to the first cutting surface 17 thereby insulating the first cutting surface 17 from the second cutting surface 19 when the jaw members 12,14 are in their closed position but which allows electrical conduction between the first and second cutting edges 16,18 when tissue is present between the cutting edges 16,18.

Furthermore, a second insulating coating 28 is secured to the second grasping surface 22 thereby insulating the first grasping surface 20 from the second grasping surface 22. A third insulating coating 34 is supplied at the first pivoting surface 30. Lastly, a fourth insulating coating 36 is provided on the rivet, pin, or screw 24, to prevent electrical conduction from the first jaw member 12 to the second jaw member 14 through the pivot rivet, screw, or pin 24.

The insulating coatings 26, 28, and 34 are preferably aluminum oxide, plasma deposited on the instrument surfaces. The thickness of the aluminum oxide coatings can be between 0.003 and 0.010 inches thick, preferably between 0.005 and 0.007 inches thick to withstand a voltage of approximately 1,500 volts.

Preferably, the pivot pin, screw, or rivet 24 is similarly coated, but also can be fabricated from a high strength polymer, a glass-filled polymer, a ceramic-filled polymer, or fabricated entirely from a ceramic. If fabricated from a ceramic, it can be further impregnated with a polymer, such as PTFE, to improve its lubricity. Additionally, the pin, screw or rivet is typically epoxied in place with any suitable medical grade epoxy.

As shown in FIGS. 3A through 3D, the second insulating coating 28 preferably covers only a portion of the second grasping surface 22. When tissue is grasped between the first grasping surface 20 and second grasping surface 22, RF energy from one jaw member will be conducted to the other in the portions of the second grasping surface 22 which are uncoated, thereby cauterizing the tissue between the grasping surfaces 20,22 in the region of the uncoated portions.

Figure 3A:
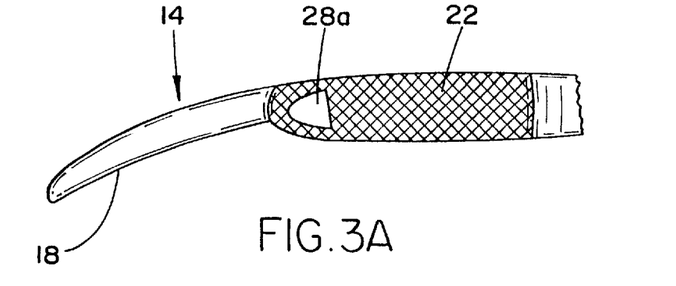
FIG. 3A illustrates a plan view of the second jaw member of the present invention as viewed along line 3—3 in FIG. 1A.
Figure 3B:
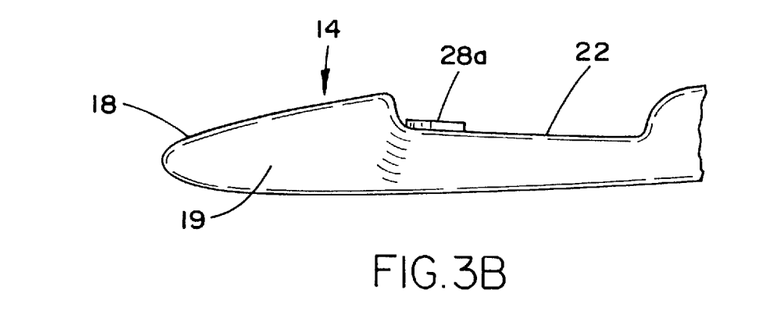
FIG. 3B illustrates a side view of the second jaw member of the present invention as illustrated in FIG. 3A.

Since the second insulating coating 28 covers only a portion of the second grasping surface 22 it can therefore take on a variety of shapes and sizes. FIG. 3A shows the second insulating coating 28a applied as a semi-circle across the width of the second grasping surface 22. The second insulating coating 28a is preferably raised above the second grasping surface 22, as shown in FIG. 3B, such that an insulating gap is maintained between the first grasping surface 20 and the second grasping surface 22 when the jaw members 12,14 are in their closed position. The insulating gap prevents electricity from being conducted from the first grasping surface 20 to the second grasping surface 22 when the jaw members 12,14 are in their closed position and tissue is not present between them.

It should be noted that the second insulating coating 28 is used to maintain an insulating gap between the first grasping surface 20 and the second grasping surface 22 equal to the thickness of the coating 28. The second insulating coating 28 can be eliminated and an insulating air gap used to isolate the first grasping surface 20 from the second grasping surface 22.

It should also be noted that the second insulating coating 28, as well as the first insulating coating 26, are not essential to the functioning of the instrument. They are provided for safety reasons to eliminate the possibility of electrical shorting between the jaw members 12,14 in the situation where the instrument is accidentally energized with RF energy while the jaw members 12,14 are in their closed position and tissue is not present between them. Such a situation where electrical shorting occurs between the jaw members 12,14 can be potentially dangerous to both the surgeon and patient.

Figure 3C:
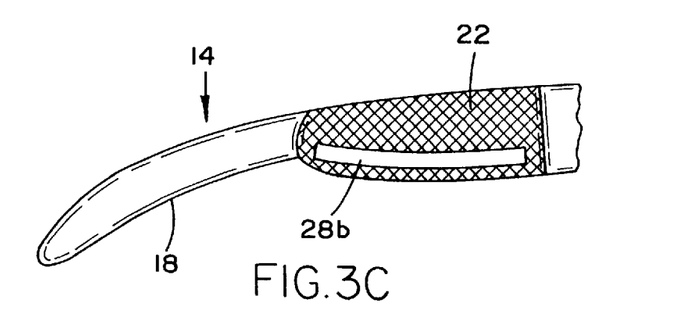
FIG. 3C illustrates a plan view of the second jaw member of an alternative version of the present invention as it would be viewed along line 3—3 in FIG. 1A.
Figure 3D:
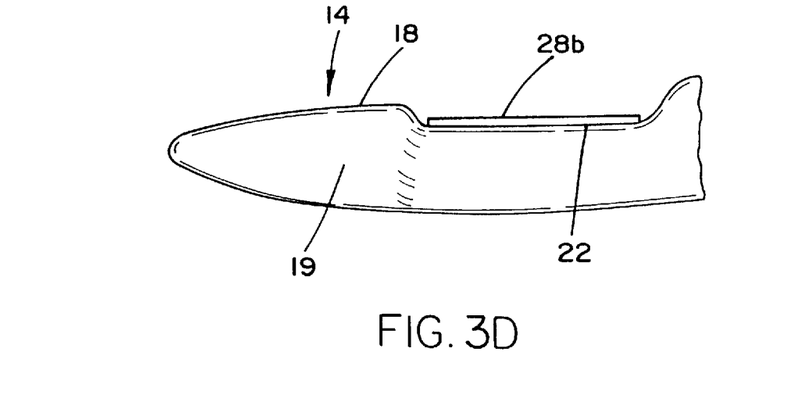
FIG. 3D illustrates a side view of the second jaw member of an alternative version of the present invention as illustrated in FIG. 3C.
Figure 4A:
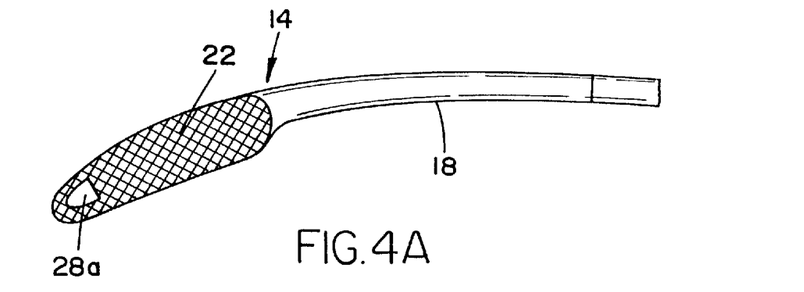
FIG. 4A illustrates a plan view of the second jaw member of the present invention as viewed along line 4—4 in FIG. 2A.
Figure 4B:
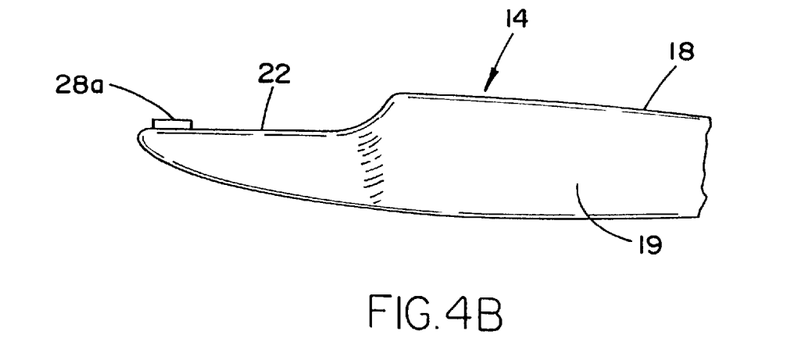
FIG. 4B illustrates a side view of the second jaw member of the present invention as illustrated in FIG. 4A.
Figure 4C:
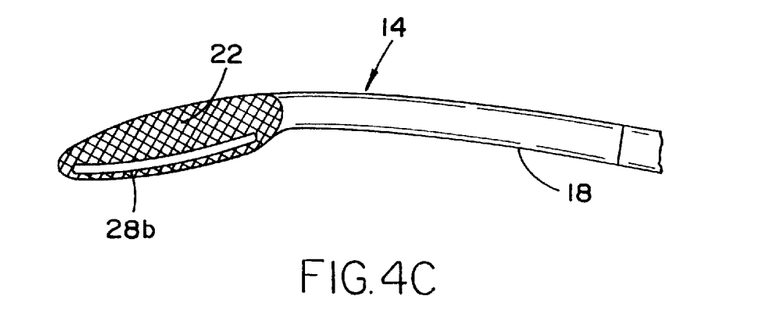
FIG. 4C illustrates a plan view of the second jaw member of an alternative version of the present invention as it would be viewed along line 4—4 in FIG. 2A.
Figure 4D:
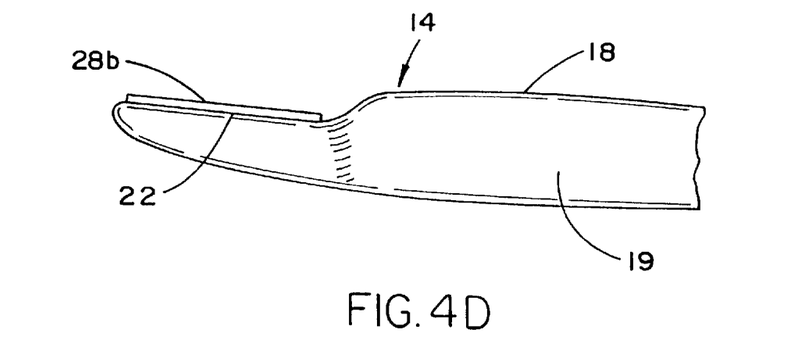
FIG. 4D illustrates a side view of the second jaw member of an alternative version of the present invention as illustrated in FIG. 4C.

Similarly, FIG. 3C shows an alternatively shaped second insulating coating 28b applied as a strip across the length of the first grasping surface 20. FIG. 3D shows that the second insulating coating 28b is likewise raised above the second grasping surface 22 such that an insulating gap is maintained between the first grasping surface 20 and the second grasping surface 22 when the jaw members 12, 14 are in their closed position.

Referring back to FIGS. 1A and 1B, as shown clearly in a comparison of FIGS. 1C and 1D, the shape of the instrument's distal end does not vary from the shape of the predetermined blade configuration of the standard scissor's blades 12a,14a even though grasping surfaces 20,22 have been formed therein. Since the grasping surfaces 20,22 follow the contours of a standard scissor shape, the feel and use of the standard scissor is maintained for the combined instrument. The grasping surfaces are formed into the jaw members of the scissors by any methods known in the art, such as grinding, machining, or casting of the jaw members having both the cutting edges and grasping surfaces formed therein. Thus, the grasping surfaces do not necessarily have to be formed after the formation of the jaw members having the cutting edges. As in the case where the jaw members are formed by casting, the cutting edges and grasping surfaces of the jaw members may be formed simultaneously. Of course, secondary operations may be necessary, such as sharpening the cutting edges and machining a knurled pattern on the grasping surfaces.

Figure 2A:
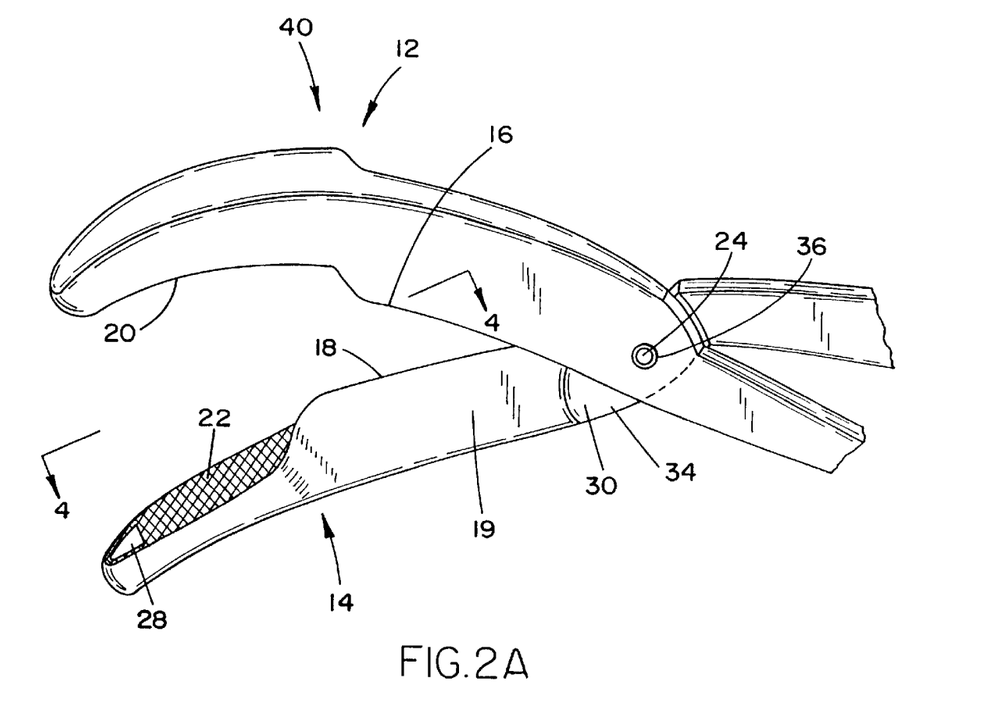
FIG. 2A illustrates an isometric view of the operating end of an embodiment of the present invention in which the graspers portion is distal, the jaw members thereof being shown in an opened position.
Figure 2B:
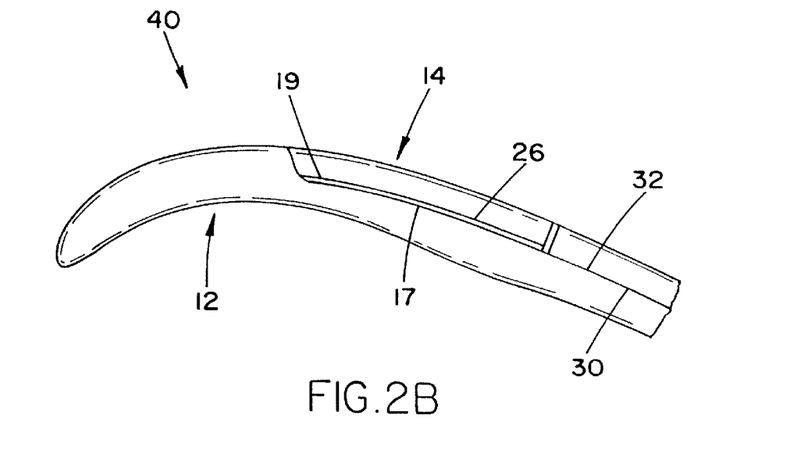
FIG. 2B illustrates the top view of the embodiment illustrated in FIG. 2A, the jaw members thereof being shown in a closed position.

FIGS. 1A and 1B illustrate an embodiment of the present invention 10 configured to have the cutting edges 16,18 distal to the grasping surfaces 20,22. FIGS. 2A and 2B illustrate a similar embodiment of the present invention 40 in which all components similar to or identical with those in FIGS. 1A and 1B are designated by the same reference numerals, and is merely modified with regard to the previous embodiment, in that the jaw members 12,14 are configured to have the grasping surfaces 20,22 distal to the cutting edges 16,18. Similarly, FIGS. 4A through 4D illustrate two variations of the second insulating surface 28a,28b similar to those previously discussed and shown in FIGS. 3A through 3D.

As shown clearly in FIG. 2B, the shape of the instrument's distal end does not vary from the shape of a standard scissor, even though grasping surfaces 20,22 have been formed therein. Since the grasping surfaces 20,22 follow the contours of a standard scissor shape, the feel and use of the standard scissor is maintained for the combined instrument. Since the width of the scissor tapers down toward the distal tip, less grasping surface is available in this configuration than in the configuration shown in FIGS. 1A and 1B. However, each configuration is useful and more effective in certain surgical procedures depending upon the cutting and grasping requirements for the procedure. As discussed previously with regard to the embodiments shown in FIGS. 1A and 1B, the grasping surfaces can be formed by any method known in the art and do not have to be formed after the formation of the jaw members having the cutting edges, but may be formed simultaneously therewith.

Figure 5A:
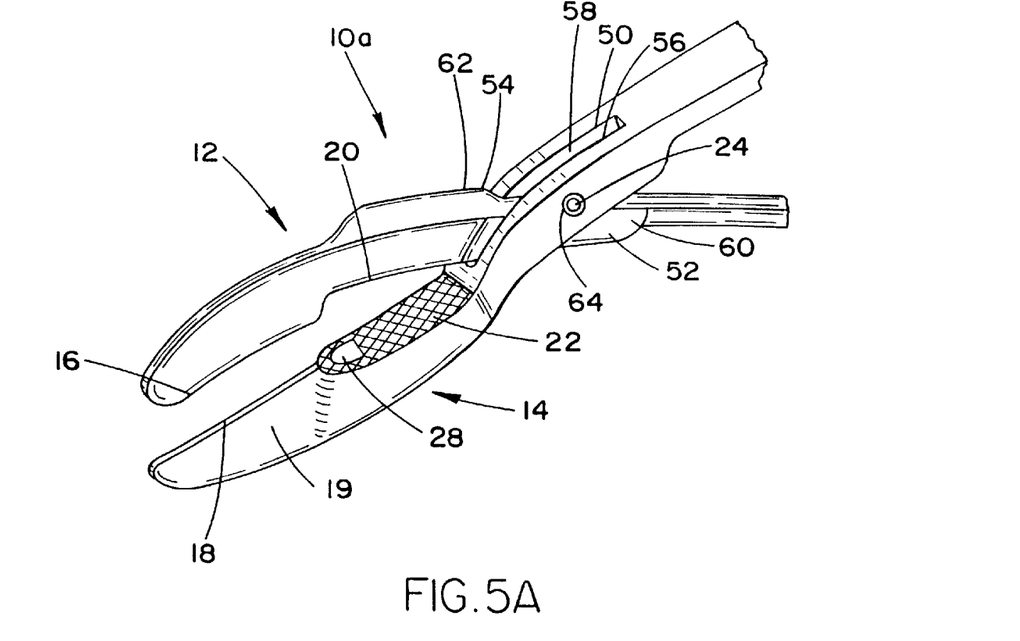
FIG. 5A illustrates a box-lock version of the present invention as shown in FIG. 1A.
Figure 5B:
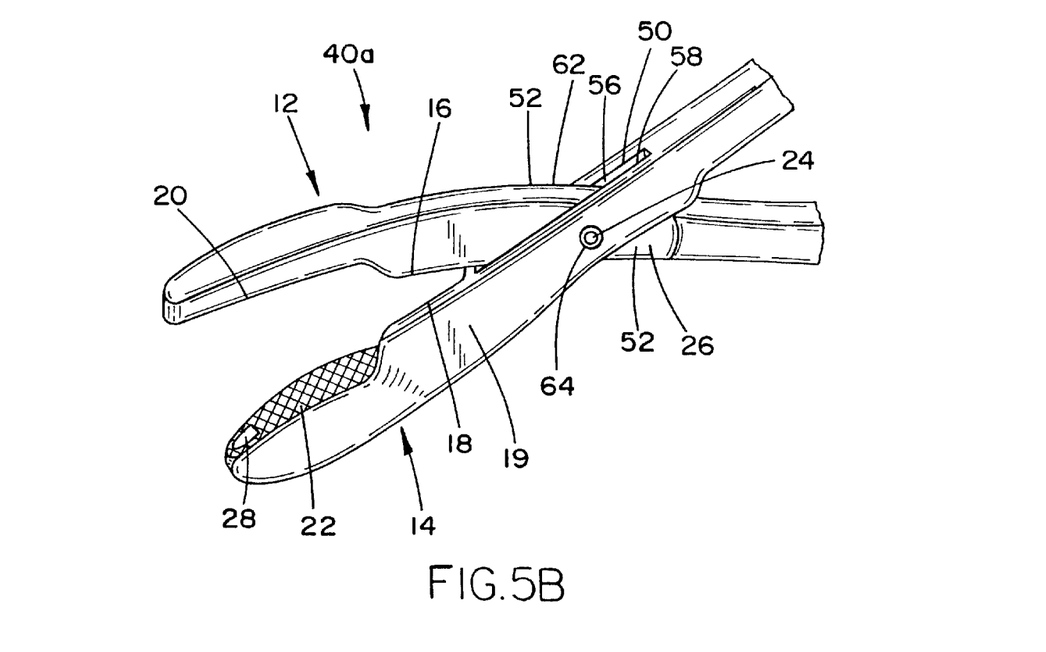
FIG. 5B illustrates a box-lock version of the present invention as shown in FIG. 2A.

Referring now to FIGS. 5A and 5B there is illustrated the embodiments of FIGS. 1A and 2A, respectively, in which the standard scissor pivot configuration is replaced by a box-lock pivot configuration. FIG. 5A illustrates an instrument 10a of the present invention configured with the scissors portion distal to the grasping portion. In the box-lock configuration shown, the first jaw member 12 is retained within, and pivots within a slot 50 disposed in the second jaw member 14. In addition, the first member 12 has a first and second pivoting surface 52,54 and the second member 14 has a third and fourth pivoting surface 56,58. The first pivoting surface 52 being in sliding contact with the third pivoting surface 56 and the second pivoting surface 54 being in sliding contact with the fourth pivoting surface 58. Third and fourth insulating coatings 60,62 are needed on the first and second pivoting surfaces 52,54 on the first jaw member 12 in order to isolate the first jaw member 12 from the second jaw member 14. A fifth insulating coating 64 is disposed around the pin, rivet, or screw 24 to complete the electrical isolation of the first jaw member 12 from the second jaw member 14. Otherwise, all components are similar to, or identical with, those in FIG. 1A and are designated with the same reference numerals.

Referring now to FIG. 5B, there is illustrated an instrument of the present invention configured with the graspers portion distal to the scissors portion, similar to the instrument shown in FIG. 2A. The instrument illustrated in FIG. 5B differs in that it replaces the conventional scissor pivoting means with a box-lock pivot means. This embodiment is similar to the embodiment shown in FIG. 5A except for the grasper portion being distal to the scissor portion. In a variation of this configuration, the first insulating coating 26 can be extended to the first pivoting surface 52, thereby eliminating the need for a separate fourth insulating coating 60. Otherwise, all components are similar to, or identical with, those in FIG. 2A and are designated with the same reference numerals.

The embodiment as configured in FIGS. 1A and 1B with the scissors portion distal to the grasping portion is preferred for procedures that require cauterization of larger vessels, or groups of vessels. It is particularly suited for procedures requiring cauterization of vessels larger than three millimeter in diameter. The coagulation of ovarian vessels in an "Oophorectomy" is representative of such a procedure.

The embodiment as configured in FIGS. 2A and 2B with the graspers portion distal to the scissors portion is preferred for those procedures requiring extensive blunt dissection. Procedures requiring separation of connective tissue to free vein and artery, such as "Pericardiectomy for Constrictive Pericarditis" and "Harvesting for a Free Greater Omentum Transfer" are examples of such procedures.

Furthermore, there are procedures where either configuration could be used, and the surgeon would want a choice of either instrument.

Mayo, Metzenbaum, and Tenotomy predetermined blade configurations have been discussed in relation to the present invention. However, it should be understood that any standard shape scissor employing a predetermined blade configuration now known or later developed can be employed in the present invention. A point of novelty, among others, thereof being the formation of grasping surfaces in a standard scissor shape whereby the contours, shape, and size of the scissor is maintained, thus preserving the same feel and use as the standard scissor. It should also be understood that any standard scissor shape used in the present invention can be configured in either a straight blade or curved blade configuration.

Figure 6:
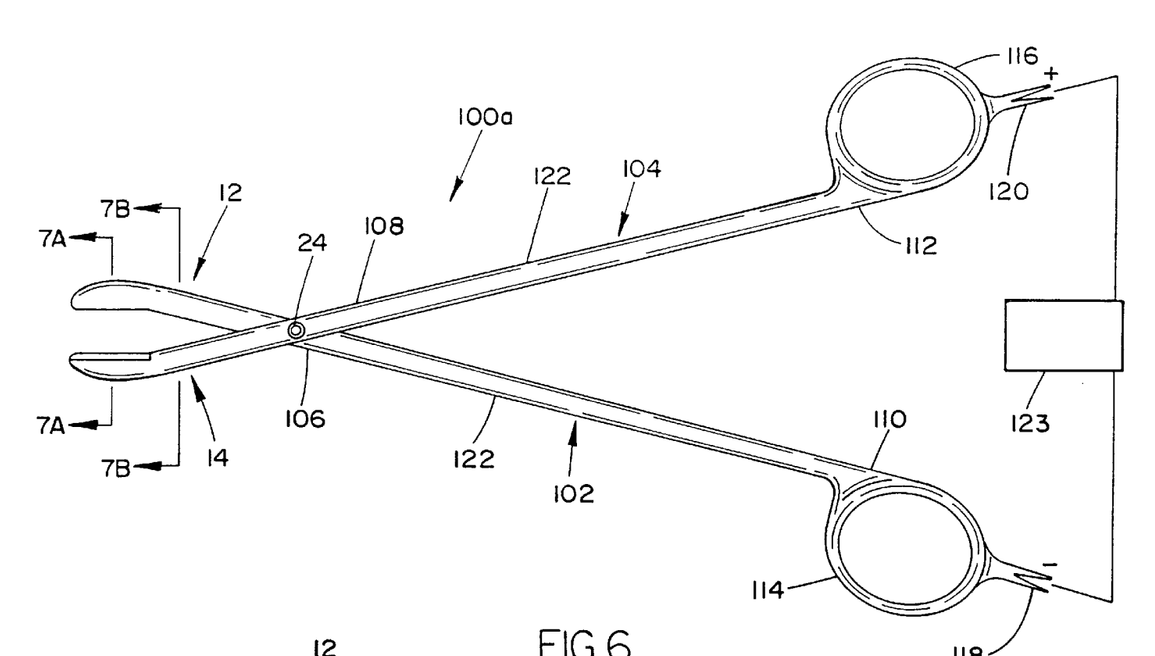
FIG. 6 illustrates the instrument of FIG. 1A with the jaw members of the instrument being shown in the open position.

Referring now to FIG. 6, the operating (or distal) end of the present invention as shown in FIGS. 1A and 1B is integral with an actuation means for opening and closing the jaw members 12,14 relative to each other resulting in an embodiment of the present invention 100a useful for open surgical procedures. In a preferred implementation, the actuation means comprises first and second conductive elongated members 102,104. Each elongated member having a distal end 106,108 and a proximal end 110,112. The first jaw member 12 being integral with the distal end 106 of the first elongated member 102. The second jaw member 14 being disposed on the distal end 108 of the second elongated member 104.

Figures 8, 9:
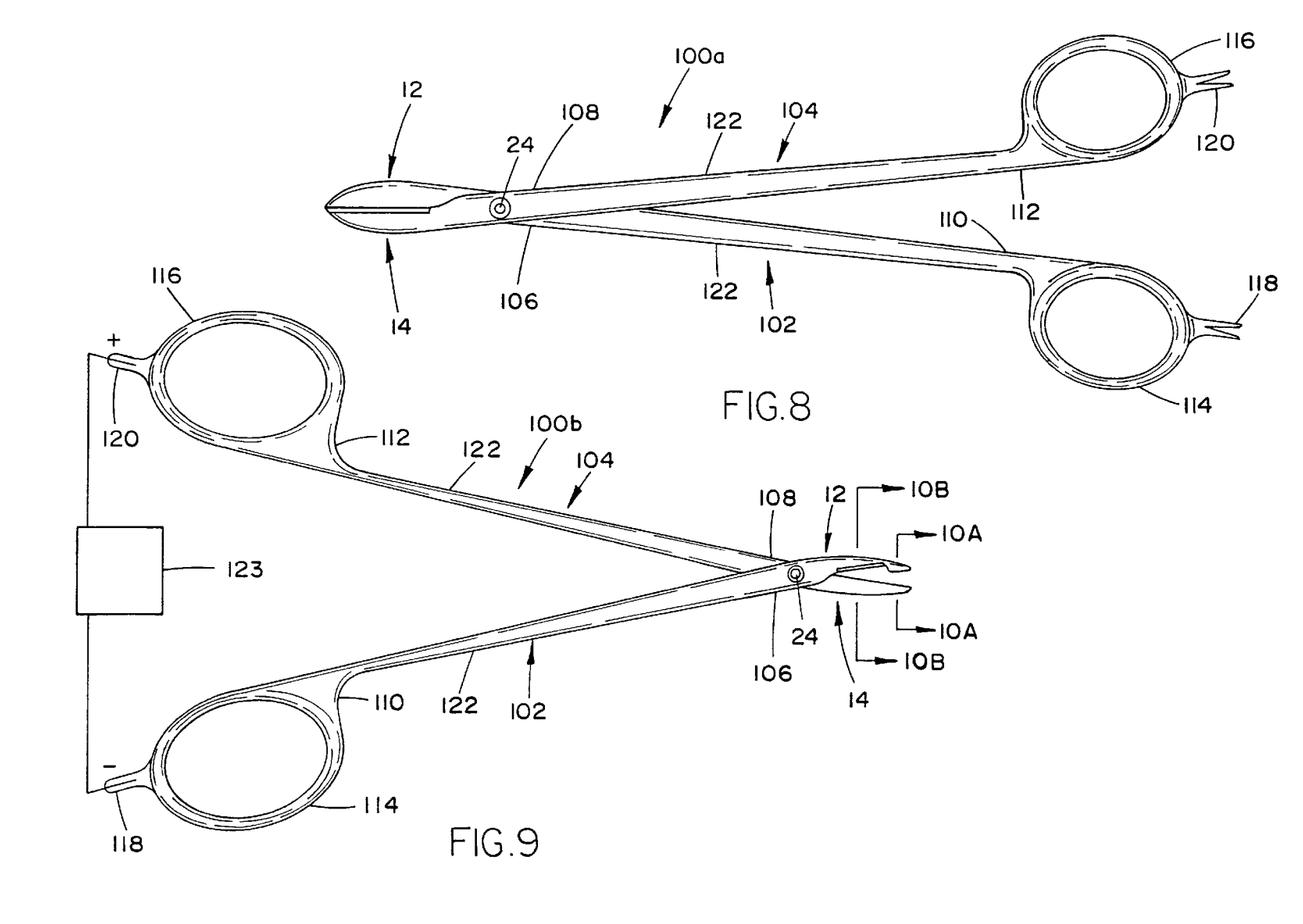
FIG. 8 illustrates the instrument of FIG. 1A with the jaw members of the instrument being shown in the closed position.
FIG. 9 illustrates the instrument of FIG. 2A with the jaw members of the instrument being shown in the open position.
Figure 10A:
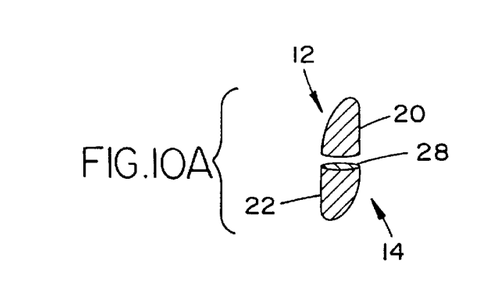
FIGS. 10A and 10B illustrate sectional views taken along lines 10A—10A and 10B—10B respectively in FIG. 9.
Figure 10B:
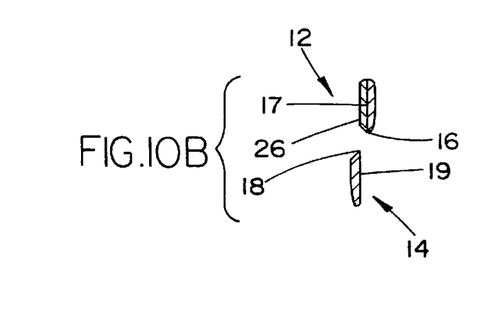
Figure 11:
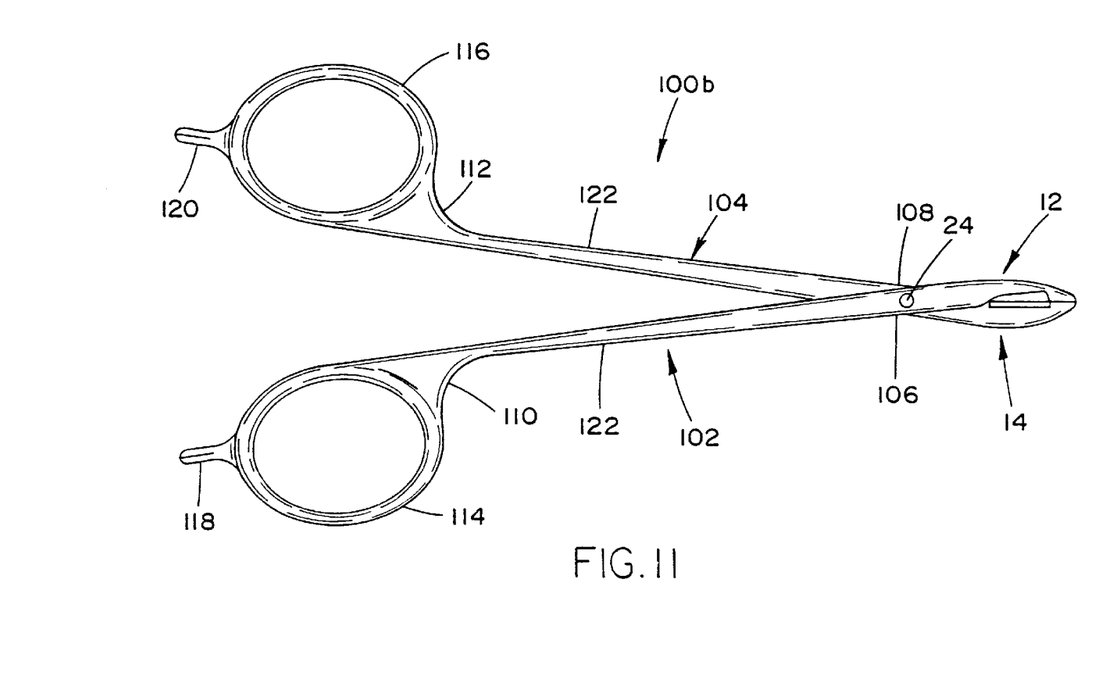
FIG. 11 illustrates the instrument of FIG. 2A with the jaw members of the instrument being shown in the closed position.

The first elongated member 102 pivots about the second elongated member 104 about the pivot pin, screw or rivet 24. First and second finger loops 114,116 are provided at the proximal ends 110,112 of the elongated members 102,104 for insertion of fingers for actuation of the jaw members 12,14 between an open position as shown in FIG. 6 and a closed position as shown in FIG. 8.

Referring back to FIG. 6, a means for supplying RF energy to the first jaw member 12 and RF energy of the opposite polarity to the second jaw member 14 is accomplished by first and second conductive connectors 118,120 disposed at the proximal ends 110,112 of the elongated members 102,104 for connection to a power cord (not shown).

The power cord typically connects to an electrosurgical generator 123 which energizes each of the electrical connectors 118,120 with RF energy used to cauterize tissue. In a bipolar configuration, the first electrical connector 118 is supplied with RF energy having a certain polarity, while the second electrical connector 120 is supplied with RF energy of the opposite polarity.

Since the electrical connectors 118,120, the elongated members 102,104, and the jaw members 12,14 are typically conductive, the RF energy is transported from the electrical connectors 118,120, through the elongated members 102, 104, to the jaw members 12,14. To protect and insulate a user from shock, the elongated members 102,104 along with the finger loops 114,116 are coated with an electrically insulating material 122, preferably nylon to prevent electrical conduction from portions of the instrument other than those intended. Typically, the insulating coating 122 extends just past the pivot pin, rivet, or screw 24 leaving only the electrical is connectors 118,120 and most of the jaw members 12,14 exposed. Since the first jaw member 12 is electrically isolated from the second jaw member 14 the RF energy supplied at electrical connector 118 will not short with the opposite polarity RF energy supplied at electrical connector 120 unless tissue is present between the jaw members 12,14 to complete their circuit.

Figure 7A:
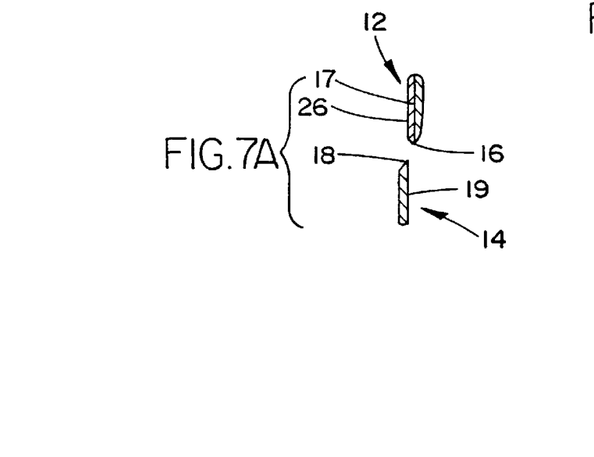
FIGS. 7A and 7B illustrate sectional views taken along lines 7A—7A and 7B—7B respectively in FIG. 6.
Figure 7B:
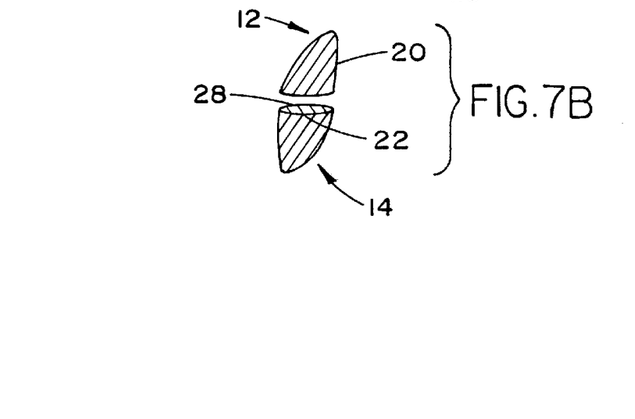

Referring now to FIGS. 7A and 7B, FIG. 7A is taken along the line 7A—7A in FIG. 6 illustrating a sectional view of cutting edges 16,18 and the insulated coating 26 secured to the first cutting edge 16. Similarly, FIG. 7B is taken along the line 7B—7B in FIG. 6 illustrating a sectional view of grasping surfaces 20,22 and the insulated coating 28 secured to the second grasping surface 22.

The embodiment shown in FIGS. 6, 7A, 7B, and 8 can also be configured in the box-lock configuration shown in FIG. 5A and in any standard scissor configuration now known or later developed in the surgical arts. Furthermore, any of these configurations can be of a reusable or disposable nature.

The embodiment illustrated in FIGS. 9, 10A, 10B, and 11, generally referred to by reference numeral 100b, in which all components similar to or identical with those in FIGS. 6, 7A, 7B, and 8 are designated with the same reference numerals, is merely modified with regard to the previous embodiment, in that the configuration of jaw members 12,14 is as shown in FIGS. 2A and 2B where the grasping surfaces 20,22 are distal to the cutting edges 16,18.

The embodiment shown in FIGS. 9, 10A, 10B, and 11 can also be configured in the box-lock configuration shown in FIG. 5B or in any standard scissor configuration now known or later developed in the surgical arts. Furthermore, any of these configurations can be of a reusable or disposable nature.

Referring now to FIGS. 12A–B to 14A–B there are illustrated plan and side views of three standard shaped surgical scissors, the shape of which are well known in the art to surgeons and others skilled in the surgical arts. While these well known surgical scissors have distinctive shapes, they can vary somewhat in scale.

Figure 13A:
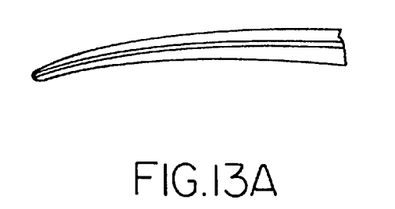
FIGS. 13A and 13B illustrate a plan and front view, respectively, of a standard Metzenbaum surgical scissor.
Figure 13B:
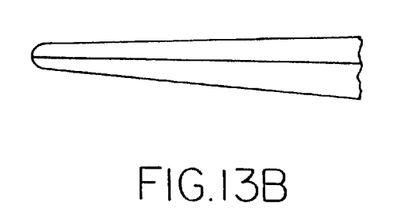
Figure 14A:
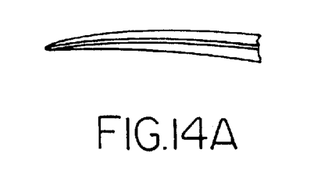
FIGS. 14A and 14B illustrate a plan and front view, respectively, of a standard Tenotomy surgical scissor.
Figure 14B:
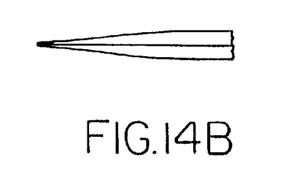

FIGS. 12A and 12B illustrate a plan and side view, respectively, of a Mayo surgical scissor, FIGS. 13A and 13B illustrate a plan and side view, respectively, of a Metzenbaum surgical scissor, and FIGS. 14A and 14B illustrate a plan and side view, respectively, of a Tenotomy surgical scissor. While the methods of the present invention are applicable to any standard shaped scissor having a predetermined blade configuration, they have been found particularly useful with the Mayo, Metzenbaum, and Tenotomy scissor blade configurations illustrated in FIGS. 12A–B to 14A–B.

From the foregoing, it becomes readily apparent to one skilled in the art that the novel combination bipolar scissors/graspers instrument offers improved coaptation of vessels and decreases the number of instruments required in surgical procedures in which both cutting and grasping is required, which renders the instrument much more effective in certain surgical procedures and much less expensive to purchase, and to process in comparison with currently employed instruments. It should also be readily apparent that the present invention, although shown with regard to an open surgical instrument, it equally applicable to endoscopic versions thereof.

Although this invention has been shown and described with respect to detailed embodiments thereof, it will be understood by those skilled in the art that various changes in form and detail thereof may be made without departing from the spirit and scope of the claimed invention.

What is claimed is:

1. A method of forming a combination bipolar scissors and graspers surgical instrument, the method comprising the steps of:
    providing a predetermined blade configuration of a bipolar scissors surgical instrument, the predetermined blade configuration having first and second jaw members each having a respective first and second cutting edge and first and second pivoting surfaces;
    defining a first grasping surface on the first jaw member, the first grasping surface being distal to the first cutting edge, the first grasping surface being contained within the confines of the predetermined blade configuration;
    defining a second grasping surface opposing the first grasping surface on the second jaw member, the second grasping surface being contained within the confines of the predetermined blade configuration;
    wherein the predetermined blade configuration conforms to the shape and dimensions of one of a standard Mayo, Metzenbaum or Tenotomy surgical scissor;
    providing a pivot pin pivotally connected to the jaw members wherein at least one jaw member is pivotable in relation to the other jaw member about the pivoting surfaces, the jaw members being capable of pivoting between an open and closed position such that the cutting edges form a scissor and the grasping surfaces form a clamp when the jaw members are in their closed position; and
    electrically isolating the first jaw member from the second jaw member.

2. The method as claimed in claim 1, wherein the providing of the pivot pin permits each jaw member to individually pivot in relation to the other jaw member about the pivot pin.

3. The method as claimed in claim 1, wherein the electrically isolating step comprises:
    disposing an electrically insulating coating on the first cutting surface such that the first cutting surface is electrically isolated from the second cutting surface when the jaw members are in their closed position but which allows electrical conduction between the first and second cutting edges when tissue is present therebetween;
    maintaining an insulating gap between the first grasping surface and second grasping surface for permitting electrical conduction between the grasping surfaces when tissue is inserted therebetween but which prevents electrical conduction between the grasping surfaces when tissue is not present therebetween;
    disposing an electrically insulating coating on one of the first or second pivoting surfaces; and
    preventing electrical conduction from the first jaw member to the second jaw member through the pivot pin.

4. The method as claimed in claim 3, wherein the if maintaining step comprises disposing an electrically insulating coating on the second grasping surface such that the first grasping surface is electrically isolated from the second grasping surface when the jaw members are in their closed position and tissue is not present therebetween, the electrically insulating coating being disposed on portions constituting less than the entire second grasping surface for permitting electrical conduction between the uncoated portions of the second grasping surface and the first grasping surface when the jaw members are in their closed position and tissue is present therebetween.

5. The method as claimed in claim 3, wherein the preventing step comprises disposing an insulating coating on the pivot pin.

6. The method as claimed in claim 3, wherein the preventing step comprises fabricating the pivot pin from an insulating material.

7. The method as claimed in claim 1, further comprising the step of preventing electrical conduction from portions of the instrument other than the first and second jaw members.

8. The method as claimed in claim 7, wherein the step of preventing electrical conduction from portions of the instrument other than the first and second jaw members comprises disposing a nylon coating on portions of the instrument other than substantially all of the first and second jaw members.

9. A method of forming a combination bipolar scissors and graspers surgical instrument, the method comprising the steps of:
    providing a predetermined blade configuration of a bipolar scissors surgical instrument, the predetermined blade configuration having first and second jaw members each having a respective first and second cutting edge and first and second pivoting surfaces;
    defining a first grasping surface on the first jaw member, the first cutting edge being distal to the first grasping surface, the first grasping surface being contained within the confines of the predetermined blade configuration;
    defining a second grasping surface opposing the first grasping surface on the second jaw member, the second grasping surface being contained within the confines of the predetermined blade configuration;

providing a pivot pin pivotally connected to the jaw members wherein at least one jaw member is pivotable in relation to the other jaw member about the pivoting surfaces, the jaw members being capable of pivoting between an open and closed position such that the cutting edges form a scissor and the grasping surfaces form a clamp when the jaw members are in their closed position; and electrically isolating the first jaw member from the second jaw member.

10. The method as claimed in claim 9, wherein the providing of the pivot pin permits each jaw member to individually pivot in relation to the other jaw member about the pivot pin.

11. The method as claimed in claim 9, wherein the electrically isolating step comprises:

disposing an electrically insulating coating on the first cutting surface such that the first cutting surface is electrically isolated from the second cutting surface when the jaw members are in their closed position but which allows electrical conduction between the first and second cutting edges when tissue is present therebetween;

maintaining an insulating gap between the first grasping surface and second grasping surface for permitting electrical conduction between the grasping surfaces when tissue is inserted therebetween but which prevents electrical conduction between the grasping surfaces when tissue is not present therebetween;

disposing an electrically insulating coating on one of the first or second pivoting surfaces; and preventing electrical conduction from the first jaw member to the second jaw member through the pivot pin.

12. The method as claimed in claim 11, wherein the maintaining step comprises disposing an electrically insulating coating on the second grasping surface such that the first grasping surface is electrically isolated from the second grasping surface when the jaw members are in their closed position and tissue is not present therebetween, the electrically insulating coating being disposed on portions constituting less than the entire second grasping surface for permitting electrical conduction between the uncoated portions of the second grasping surface and the first grasping surface when the jaw members are in their closed position and tissue is present therebetween.

13. The method as claimed in claim 11, wherein the preventing step comprises disposing an insulating coating on the pivot pin.

14. The method as claimed in claim 11, wherein the preventing step comprises fabricating the pivot pin from an insulating material.

15. The method as claimed in claim 9, further comprising the step of preventing electrical conduction from portions of the instrument other than the first and second jaw members.

16. The method as claimed in claim 15, wherein the step of preventing electrical conduction from portions of the instrument other than the first and second jaw members comprises disposing a nylon coating on portions of the instrument other than substantially all of the first and second jaw members.

17. A combination bipolar scissors and graspers surgical instrument comprising:

a first jaw member having a first cutting edge, a first cutting surface, and a first grasping surface, the first cutting edge being distal to the first grasping surface, the first jaw member further having a first pivoting surface;

a second jaw member having a second cutting edge and second cutting surface opposing the first cutting edge and first cutting surface, the second jaw member further having a second grasping surface opposing the first grasping surface and a second pivoting surface opposing the first pivoting surface and in sliding contact therewith;

a pivot pin pivotally connected to the jaw members wherein at least one jaw member is pivotable in relation to the other jaw member about the pivoting surfaces, the jaw members being capable of pivoting between an open and closed position such that the cutting edges form a scissor and the grasping surfaces form a clamp when the jaw members are in their closed position;

means for supplying electrical energy to the first jaw member and electrical energy of the opposite polarity to the second jaw member for cauterizing tissue therebetween;

isolating means for electrically isolating the first jaw member from the second jaw member; and actuation means for actuating the jaw members between their open and closed positions;

wherein the grasping surfaces are contained within the shape and size of a standard Mayo surgical scissor.

18. A combination bipolar scissors and graspers surgical instrument comprising:

a first jaw member having a first cutting edge, a first cutting surface, and a first grasping surface, the first grasping surface being distal to the first cutting edge, the first jaw member further having a first pivoting surface;

a second jaw member having a second cutting edge and second cutting surface opposing the first cutting edge and first cutting surface, the second jaw member further having a second grasping surface opposing the first grasping surface and a second pivoting surface opposing the first pivoting surface and in sliding contact therewith;

a pivot pin pivotally connected to the jaw members wherein at least one jaw member is pivotable in relation to the other jaw member about the pivoting surfaces, the jaw members being capable of pivoting between an open and closed position such that the cutting edges form a scissor and the grasping surfaces form a clamp when the jaw members are in their closed position;

means for supplying electrical energy to the first jaw member and electrical energy of the opposite polarity to the second jaw member for cauterizing tissue therebetween;

isolating means for electrically isolating the first jaw member from the second jaw member; and actuation means for actuating the jaw members between their open and closed positions;

wherein the grasping surfaces are contained within the shape and size of a standard Mayo surgical scissor.

19. A combination bipolar scissors and graspers surgical instrument comprising:

a first jaw member having a first cutting edge, a first cutting surface, and a first grasping surface, the first cutting edge being distal to the first grasping surface, the first jaw member further having a first pivoting surface;

a second jaw member having a second cutting edge and second cutting surface opposing the first cutting edge and first cutting surface, the second jaw member further having a second grasping surface opposing the first grasping surface and a second pivoting surface opposing the first pivoting surface and in sliding contact therewith;

a pivot pin pivotally connected to the jaw members wherein at least one jaw member is pivotable in relation to the other jaw member about the pivoting surfaces, the jaw members being capable of pivoting between an open and closed position such that the cutting edges form a scissor and the grasping surfaces form a clamp when the jaw members are in their closed position;

means for supplying electrical energy to the first jaw member and electrical energy of the opposite polarity to the second jaw member for cauterizing tissue therebetween;

isolating means for electrically isolating the first jaw member from the second jaw member; and actuation means for actuating the jaw members between their open and closed positions;

wherein the grasping surfaces are contained within the shape and size of a standard Metzenbaum surgical scissor.

20. A combination bipolar scissors and graspers surgical instrument comprising:

a first jaw member having a first cutting edge, a first cutting surface, and a first grasping surface, the first grasping surface being distal to the first cutting edge, the first jaw member further having a first pivoting surface;

a second jaw member having a second cutting edge and second cutting surface opposing the first cutting edge and first cutting surface, the second jaw member further having a second grasping surface opposing the first grasping surface and a second pivoting surface opposing the first pivoting surface and in sliding contact therewith;

a pivot pin pivotally connected to the jaw members wherein at least one jaw member is pivotable in relation to the other jaw member about the pivoting surfaces, the jaw members being capable of pivoting between an open and closed position such that the cutting edges form a scissor and the grasping surfaces form a clamp when the jaw members are in their closed position;

means for supplying electrical energy to the first jaw member and electrical energy of the opposite polarity to the second jaw member for cauterizing tissue therebetween;

isolating means for electrically isolating the first jaw member from the second jaw member; and actuation means for actuating the jaw members between their open and closed positions;

wherein the grasping surfaces are contained within the shape and size of a standard Metzenbaum surgical scissor.

21. A combination bipolar scissors and graspers surgical instrument comprising:

a first jaw member having a first cutting edge, a first cutting surface, and a first grasping surface, the first cutting edge being distal to the first grasping surface, the first jaw member further having a first pivoting surface;

a second jaw member having a second cutting edge and second cutting surface opposing the first cutting edge and first cutting surface, the second jaw member further having a second grasping surface opposing the first grasping surface and a second pivoting surface opposing the first pivoting surface and in sliding contact therewith;

a pivot pin pivotally connected to the jaw members wherein at least one jaw member is pivotable in relation to the other jaw member about the pivoting surfaces, the jaw members being capable of pivoting between an open and closed position such that the cutting edges form a scissor and the grasping surfaces form a clamp when the jaw members are in their closed position;

means for supplying electrical energy to the first jaw member and electrical energy of the opposite polarity to the second jaw member for cauterizing tissue therebetween;

isolating means for electrically isolating the first jaw member from the second jaw member; and actuation means for actuating the jaw members between their open and closed positions;

wherein the grasping surfaces are contained within the shape and size of a standard Tenotomy surgical scissor.

22. A combination bipolar scissors and graspers surgical instrument comprising:

a first jaw member having a first cutting edge, a first cutting surface, and a first grasping surface, the first grasping surface being distal to the first cutting edge, the first jaw member further having a first pivoting surface;

a second jaw member having a second cutting edge and second cutting surface opposing the first cutting edge and first cutting surface, the second jaw member further having a second grasping surface opposing the first grasping surface and a second pivoting surface opposing the first pivoting surface and in sliding contact therewith;

a pivot pin pivotally connected to the jaw members wherein at least one jaw member is pivotable in relation to the other jaw member about the pivoting surfaces, the jaw members being capable of pivoting between an open and closed position such that the cutting edges form a scissor and the grasping surfaces form a clamp when the jaw members are in their closed position;

means for supplying electrical energy to the first jaw member and electrical energy of the opposite polarity to the second jaw member for cauterizing tissue therebetween;

isolating means for electrically isolating the first jaw member from the second jaw member; and actuation means for actuating the jaw members between their open and closed positions;

wherein the grasping surfaces are contained within the shape and size of a standard Tenotomy surgical scissor.

* * * * *